(12) United States Patent
Cocaud et al.

(10) Patent No.: US 10,167,100 B2
(45) Date of Patent: Jan. 1, 2019

(54) PACKAGE CONTAINING A COSMETIC PRODUCT

(71) Applicant: L'OREAL, Paris (FR)

(72) Inventors: Olivier Cocaud, Paris (FR); Frank Cannarozzo, Aulnay sous Bois (FR); Jean-Marie Julien, Marly-le-Roi (FR); Patrick Charnay, Polliat (FR); Laurence Joly, Orry la Ville (FR); Nathalie Scouarnec, Paris (FR); Kerem Aubret, Paris (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/105,677

(22) PCT Filed: Dec. 19, 2014

(86) PCT No.: PCT/EP2014/078784
§ 371 (c)(1),
(2) Date: Jun. 17, 2016

(87) PCT Pub. No.: WO2015/091973
PCT Pub. Date: Jun. 25, 2015

(65) Prior Publication Data
US 2016/0311566 A1    Oct. 27, 2016

(30) Foreign Application Priority Data

Dec. 19, 2013   (FR) ........................... 13 62985
Dec. 19, 2013   (FR) ........................... 13 63090

(51) Int. Cl.
*B65B 55/14*    (2006.01)
*A45D 40/00*    (2006.01)
(Continued)

(52) U.S. Cl.
CPC .............. *B65B 55/14* (2013.01); *A45D 34/02* (2013.01); *A45D 40/0068* (2013.01);
(Continued)

(58) Field of Classification Search
CPC ..... B65B 55/14; B65B 55/06; A45D 40/0075; A61L 2202/23
See application file for complete search history.

(56) References Cited

U.S. PATENT DOCUMENTS 5,573,043 A * 11/1996 Fuehrer ................. B65B 31/003
                                                                141/20
2005/0258172 A1  11/2005 Gueret
(Continued)

FOREIGN PATENT DOCUMENTS

FR   2946248 A1   12/2010
GB   1326631 A    8/1973
(Continued)

OTHER PUBLICATIONS

English Translation of Publication No. FR 2946248 (A1) provided by Espacenet; Rossow, Jean; Sterilizing cosmetic product comprises incorporating product in soft, oxygen proof packaging and resistant to specific temperature, removing air located in the packaging, tight sealing packaging and heating filled and closed packaging; Dec. 10, 2010.*

(Continued)

*Primary Examiner* — Kevin Joyner
(74) *Attorney, Agent, or Firm* — Polsinelli PC

(57) ABSTRACT

The invention relates to a package (10) containing a cosmetic product (12), the package comprising a basic body (14), a neck (18) and a closure member or product dispensing member (20) mounted on the neck (18), so as to form an internal volume (16) containing the cosmetic product.
According to the invention, the package resists an increase in pressure of at least 0.245 bar within the internal volume (Continued)

(16) together with a rise in the temperature of the product to above 85° C., in particular between 85° C. and 150° C.

25 Claims, 3 Drawing Sheets

(51) Int. Cl.
*B65B 55/06* (2006.01)
*A45D 34/02* (2006.01)
*A61L 2/00* (2006.01)
*B65B 55/02* (2006.01)

(52) U.S. Cl.
CPC ........ *A45D 40/0075* (2013.01); *A61L 2/0064* (2013.01); *B65B 55/06* (2013.01); *A45D 2200/05* (2013.01); *A45D 2200/25* (2013.01); *A61L 2202/23* (2013.01); *B65B 55/02* (2013.01)

(56) References Cited

U.S. PATENT DOCUMENTS

| | | |
|---|---|---|
| 2011/0226792 A1* | 9/2011 | Lasfargues ............ B65D 35/12 220/837 |
| 2012/0196011 A1 | 8/2012 | Felix |
| 2013/0004230 A1 | 1/2013 | Kirk et al. |
| 2013/0161345 A1 | 6/2013 | Tatin |

FOREIGN PATENT DOCUMENTS

| | | |
|---|---|---|
| JP | H-07156933 A | 6/1995 |
| JP | 2002012277 A | 1/2002 |
| WO | WO-9913741 A1 | 3/1999 |
| WO | WO-2013089054 A1 | 6/2013 |

OTHER PUBLICATIONS

Mikell Knights, "Microwave sterilization for packaged meals", URL:http://www.microwaveheating.wsu.edu/news/files/Microwave_sterilization_for_packaged_meals.pdf, retrieved Sep. 2, 2014.

\* cited by examiner

PACKAGE CONTAINING A COSMETIC PRODUCT

CROSS REFERENCE TO RELATED APPLICATIONS

This application is a National Phase filing under 35 U.S.C. § 371 of PCT/EP2014/078784 filed on Dec. 19, 2016; and this application claims priority to Application No. 1362985 filed in France on Dec. 19, 2013 under 35 U.S.C. § 119; and this application claims priority to Application No. 1363090 filed in France on Dec. 19, 2013 under 35 U.S.C. § 119. The entire contents of each application are hereby incorporated by reference.

The present invention relates to a package containing a cosmetic product and to a process for decontaminating and packaging a cosmetic product.

The term "decontamination" is understood to mean pasteurization or sterilization of the cosmetic product.

The expression "cosmetic product" is understood, in particular within the meaning of the present invention, to mean a product as defined in Regulation (EC) No 1223/2009 of the European Parliament and Council of 30 Nov. 2009 relating to cosmetic products.

The product may be in any possible form, in particular a solution, gel, or emulsion and may contain fillers, pigments, different oil contents etc.

The cosmetic product is advantageously a composition intended to be applied to the skin, for example a care composition for the skin or a cleansing composition for the skin.

The most common technique for decontaminating a cosmetic product composition consists in adding one or more chemical preservative(s), such as parabens, for example, to the composition. This prevents microbial development, both during the product production phase and throughout the period of use of this product and guarantees quality for the consumer.

However, some of these chemical preservatives have drawbacks on account of their high penetrating power, their persistence or because they can cause allergic reactions. There is thus a need for solutions for protecting cosmetic products that do not involve the presence of chemical preservatives in the composition.

In order to meet this need, the prior art discloses a process for decontaminating a cosmetic product that consists in adding to the composition of the product ingredients that have antimicrobial activity but are not listed as "preservatives" in the annex to Regulation (EC) No 1223/2009 of the European Parliament and Council of 30 Nov. 2009 relating to cosmetic products.

However, such replacement ingredients have weaker antimicrobial activity than that of the chemical preservatives, in particular parabens.

Further processes for decontaminating cosmetic products are known. Some of these processes consist in manufacturing the products under pharmaceutical manufacturing conditions, that is to say carrying out a prior thermal treatment of the products in bulk form, then separately treating the articles for packaging these products and then packaging the products in a clean room and under a controlled atmosphere. However, such processes involve high costs and significant manufacturing constraints.

Thus, a real problem facing the industry today is the creation of a possibility for better protection of cosmetic products, which does not have drawbacks for consumers' bodies and can be industrialized easily.

It is an aim of the invention to propose a package suitable for a process for decontaminating a cosmetic product that makes it possible to obtain effective decontamination without having drawbacks for consumers' bodies, while being easy to industrialize, and having increased resistance to temperatures, microwaves and internal pressures generated by the heating of the cosmetic product it contains.

A subject of the invention is a package containing a cosmetic product, the package comprising a basic body, a neck and a closure member or product dispensing member mounted on the neck, so as to form an internal volume containing the cosmetic product.

According to the invention, the package resists an increase in pressure of at least 0.245 bar within the internal volume together with a rise in the temperature of the product to above 85° C., in particular between 85° C. and 150° C.

According to further advantageous aspects of the invention, the package comprises one or more of the following features.

The basic body may have a dielectric constant less than 4, preferably between 2.0 and 2.6.

The basic body may have a dielectric loss factor less than $10^{-2}$, preferably between $10^{-4}$ and $10^{-3}$.

It is possible for the cosmetic product to contain no preserving agents.

The package may be rigid.

In this case, the basic body may exhibit symmetry of revolution about a central axis X-X', in particular so as to have a cylindrical, concave, convex, annular or spherical shape, as mentioned before, the package may be rigid.

The basic body may have an oval cross section the maximum diameter of which is less than or equal to 1.15 times the minimum diameter, as mentioned before, the package may be rigid.

The basic body may be provided with a substantially concave or substantially convex base, the thickness of the lateral region, located next to the base, of the basic body being advantageously greater than the thickness of the central region of the basic body, as mentioned before, the package may be rigid.

The thickness of the base may be greater than 0.5 mm, in particular greater than 0.8 mm as mentioned before, the package may be rigid.

The base may be convex as seen from the inside of the basic body, the maximum depth of the base, measured from the supporting surface of the basic body towards the inside along the axis X-X', being greater than or equal to 0.02 times the minimum diameter of the cross section of the basic body.

The package may comprise a shoulder joining the basic body to the neck, the shoulder having a substantially rounded or frustoconical shape, the thickness of the shoulder being advantageously greater than the thickness of the central region of the basic body, as mentioned before, the package may be rigid.

The basic body may then be composed of one or more materials chosen from polyolefins, polyesters, cycloolefin copolymers, polyamides, polycarbonates, polymethylpentene (TPX), polyether ether ketone (PEEK), polytetrafluoroethylene, or glass, as mentioned before, the package may be rigid.

The package may be flexible.

In this case, the basic body may be formed from a material comprising a number of layers, the thickness of each layer being between 7 μm and 300 μm, as mentioned before, the package may be flexible.

The basic body may then be composed of one or more materials chosen from polyolefins, polyesters, or polyamides, as mentioned before, the package may be flexible.

A further subject of the invention is a process for decontaminating this package containing a cosmetic product, in particular a process for pasteurizing or sterilizing, comprising the following steps of:
- providing a package containing a cosmetic product, the package being in particular as described above,
- placing the package containing the cosmetic product in a microwave cavity,
- raising the temperature of the cosmetic product contained in the package to a decontamination temperature by microwave heating, and
- keeping the cosmetic product contained in the package at the decontamination temperature for a decontamination time suitable for reducing the number of bacteria present in the cosmetic product to below a decontamination threshold, in particular a pasteurization or sterilization threshold.

In another aspect of the invention a subject of the invention is a process for decontaminating cosmetic products, in particular for pasteurizing or sterilizing, comprising the following steps of:
- providing the cosmetic product in a package,
- placing the package containing the cosmetic product in a microwave cavity,
- raising the temperature of the cosmetic product contained in the package to a decontamination temperature by microwave heating, and
- keeping the cosmetic product contained in the package at the decontamination temperature for a decontamination time suitable for reducing the number of bacteria present in the cosmetic product to below a decontamination threshold, in particular a pasteurization or sterilization threshold.

According to further advantageous aspects of the invention, the process comprises one or more of the following features:
- during the step of keeping the cosmetic product contained in the package at the decontamination temperature, a fluid is set into circulation inside the microwave cavity, the fluid being kept at the decontamination temperature by fluid heating means located within the microwave cavity;
- during the step of keeping the cosmetic product contained in the package at the decontamination temperature, a fluid is set into circulation inside the microwave cavity, the fluid being kept at the decontamination temperature by fluid heating means located outside the microwave cavity;
- the step of keeping the cosmetic product contained in the package at the decontamination temperature includes, advantageously at the same time as the setting of the fluid into circulation inside the microwave cavity, the application of a microwave heating;
- the process further includes a step of forced cooling of the cosmetic product, by introducing the package containing the cosmetic product into a cooling cell;
- the decontamination temperature is greater than or equal to 70° C., preferably greater than or equal to 85° C., preferably between 85° C. and 150° C.;
- the cosmetic product is devoid of a preservative;
- the package is sealed prior to the step of placing in the microwave cavity.

A further subject of the invention is a kit for decontaminating in particular for pasteurizing or sterilizing, and packaging a cosmetic product comprising:
- a plurality of packages filled with cosmetic product;
- a decontamination apparatus, in particular for pasteurizing or sterilizing, comprising a microwave cavity suitable for receiving each package in succession or a plurality of packages at the same time;
- a microwave cavity control assembly suitable for controlling the microwave cavity in order to effect a rise in temperature of the cosmetic product contained in each package by microwave heating to a decontamination temperature, and then to keep the cosmetic product contained in each package at the decontamination temperature for a decontamination time suitable for reducing the number of bacteria present in the cosmetic product to below a decontamination threshold, in particular a pasteurization or sterilization threshold.

A further subject of the invention is a package containing a cosmetic product, characterized in that the cosmetic product is decontaminated, in particular is pasteurized and sterilized, the decontaminated cosmetic product being suitable for being obtained using the process described above.

According to further advantageous aspects of the invention, the package comprises one or more of the following features:
- it comprises a basic body having a dielectric constant less than 4, preferably between 2.0 and 2.6;
- it comprises a basic body having a dielectric loss factor less than $10^{-2}$, preferably between $10^{-4}$ and $10^{-3}$;
- the cosmetic product is devoid of a preservative.

The invention will be better understood from reading the following description, given solely by way of example, and with reference to the appended drawings, in which.

Figure 1:
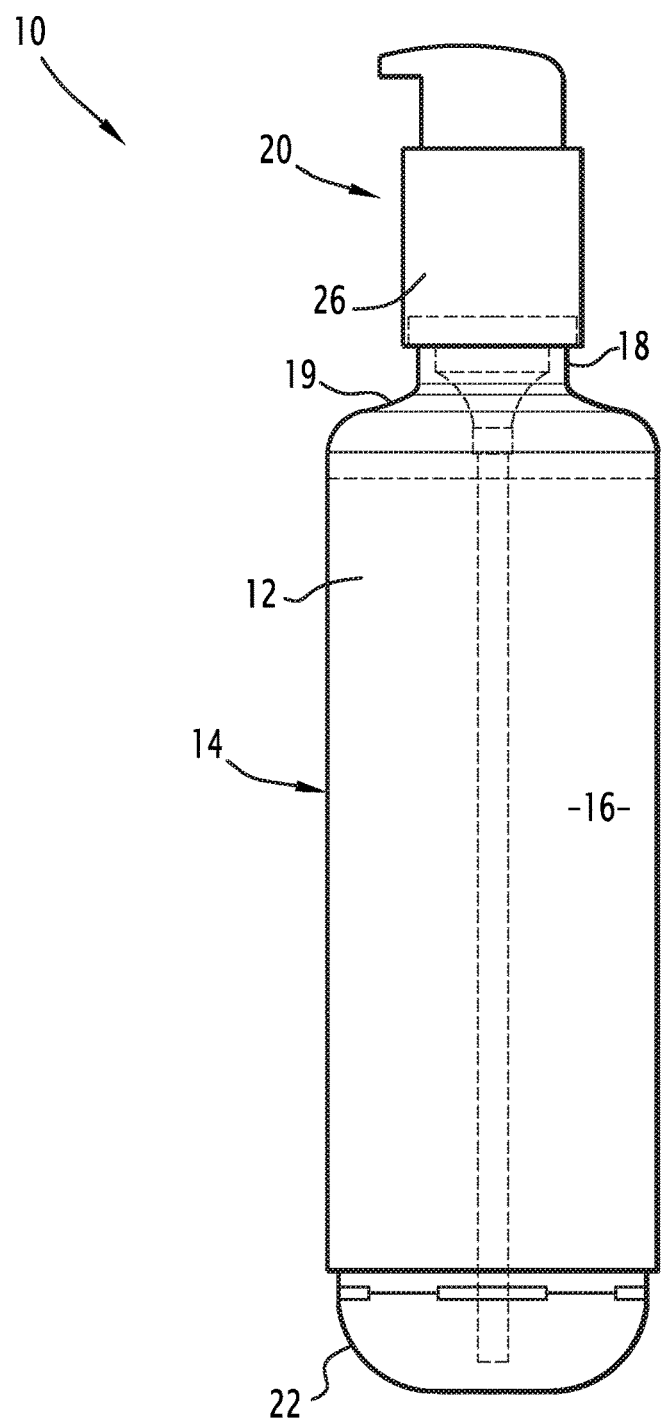
FIG. 1 is a side view of a package according to the invention.

An example of a package 10 according to the invention, containing a cosmetic product 12, is illustrated in side view in FIG. 1.

Such a cosmetic product 12 is, for example, a cleansing composition for the skin, in particular a makeup removal lotion.

Advantageously, the cosmetic product 12 is a decontaminated, in particular pasteurized or sterilized, cosmetic product obtained by implementing a decontamination process, in particular a process for pasteurizing or sterilizing and packaging in accordance with the invention, as described in detail below.

The cosmetic product 12 advantageously contains no preserving agents whatsoever. To this end, it does not comprise agents defined in Regulation (EC) No 1223/2009 of the European Parliament and Council of 30 Nov. 2009 relating to cosmetic products.

In a variant or in addition, the product 12 comprises less than 10% by weight of antimicrobial agents such as ethanol, or less than 5% by weight of antimicrobial agents, or even does not contain any antimicrobial agents at all.

The term "decontaminated" should be understood as meaning in particular that the content of bacteria is less than 1000 CFU/g, this threshold being an example of a decontamination threshold.

The term "pasteurized" should be understood as meaning that the content of bacteria of the mesophilic aerobic microorganism type and of the yeast and mould type is in each case less than 1000 CFU/g for cosmetics away from the eyes and in each case less than 100 CFU/g for sensitive products intended for the contours of the eyes and for babies.

These thresholds are determined for example by the standards ISO21149 and ISO16212.

Furthermore, no pathogenic germs of the *Candida albicans, Escherichia coli, Pseudomona aeruginosa,* or *Staphyloccocus aureus* type are present in at least one gram of product.

Advantageously, this absence is measured in each case by the standards ISO18416, ISO18415, ISO22717, and ISO22718.

These conditions define a pasteurization threshold.

The term "sterilized" should be understood as meaning that the content of bacteria is less than 1 CFU/g. These conditions define a sterilization threshold.

The package 10 comprises a basic body 14 delimiting an internal volume 16, a neck 18, and a shoulder 19 joining the basic body 14 to the neck 18.

The cosmetic product 12 is contained inside the basic body 14, within the internal volume 16. The package 10 also comprises a product dispensing member 20 mounted on the neck 18.

In the advantageous exemplary embodiment in FIG. 1, the package 10 is a rigid package of which the basic body 14 is made for example of glass and which is able to allow a number of doses of cosmetic product 12 to be dispensed to at least one user.

The expression "rigid package" should be understood as meaning any package that is advantageously non-deformable to the touch. For example, the basic body 14 is formed of a thermoplastic resin, the thermoplastic resin being a thermoplastic polyolefin such as polypropylene or high-density polyethylene, for example. In a variant, the thermoplastic resin is a cycloolefin copolymer.

In this exemplary embodiment, the cosmetic product 12 takes up a volume of advantageously greater than 50% of the internal volume 16, preferably substantially between 70% and 95% of the internal volume 16, within the basic body 14.

The basic body 14 advantageously has a dielectric constant less than 4, preferably less than 2.6.

The basic body 14 advantageously has a dielectric loss factor less than $10^{-2}$.

The basic body 14 is advantageously provided with a base 22 that has a substantially concave shape. The concave shape of the base 22 makes it possible to locally reinforce the basic body 14 and thereby to improve the pressure resistance of the basic body 14. In a variant, the shape of the base may be convex.

The concave base 22 advantageously has an increased thickness of material compared with the thickness of or the quantity of material in the rest of the basic body 14. The thickness of the base is for example greater than 0.5 mm, in particular greater than 0.8 mm.

Preferably, the internal volume 16 is between 10 ml and 250 ml. In the exemplary embodiment in FIG. 1, the internal volume 16 is substantially equal to 177 ml.

The shoulder 19 forms a joint between the basic body 14 and the neck 18. In other words, the basic body 14, the shoulder 19 and the neck 18 are formed integrally. In the advantageous exemplary embodiment in FIG. 1, the shoulder 19 has a substantially rounded shape. In a variant that is not shown, the shoulder 19 has a substantially frustoconical shape.

The substantially rounded or frustoconical shape of the shoulder 19 reinforces the basic body 14 and thereby improves the pressure resistance of the basic body 14.

In the exemplary embodiment in FIG. 1, the dispensing member 20 advantageously comprises a sealed pump 26 intended to allow a user to remove and dispense a dose of cosmetic product 12 while preserving the sealing with respect to back-contamination inside the internal volume 16.

The sealed pump 26 is for example of the "APF+" type sold by the company Aptar.

In a variant, the basic body may be closed by any sealed closure member such as a cap, for example, screwed or snap-fastened onto the basic body.

By virtue of the abovementioned features, the package 10 according to the invention is advantageously able to resist an increase in pressure of at least 0.245 bar within the internal volume 16; for example the package undergoes no deformation or irreversible distortion as a result of this increase in pressure, in particular together with an increase in temperature.

Figure 4:
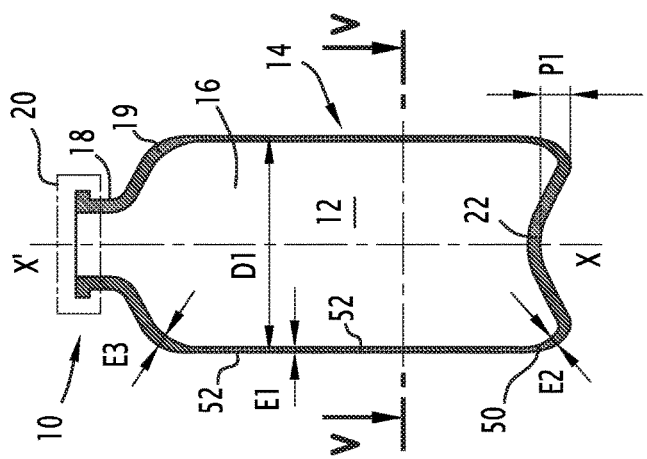
FIG. 4 illustrates a sectional view along an axial median plane of another package according to the invention.

In the variant shown in FIG. 4, the basic body 14 exhibits symmetry of revolution about a central axis X-X'. Advantageously, it has a cylindrical, concave, convex, annular or spherical shape.

It has a circular or oval cross section. In the case of an oval section, illustrated in FIG. 5, the maximum diameter D2 is advantageously less than or equal to 1.15 times the minimum diameter D1.

In this variant, the base 22 of the basic body 14 is convex to the left, as seen from the internal volume 16. The maximum depth P1 of the base 22, measured from the supporting surface of the basic body 14 towards the inside along the axis X-X' is thus advantageously greater than or equal to 0.02 times the minimum diameter D1.

In order to ensure good mechanical integrity, the maximum thickness E2 of the lateral region 50 located next to the base 22 between the supporting surface of the basic body 14 and the central region 52 of diameter D1 is greater than 1.2 times the thickness E1 in the central region 52 of diameter D1.

Preferably, the maximum thickness E3 of the shoulder 19 located between the foot of the neck 18 and the central region 52 is greater than or equal to 1.2 times the maximum thickness E1 in the central region 52, when a snap-fastened pump is mounted on the neck 18, and is greater than or equal to the thickness E1 with a screwed pump.

The internal volume 16 of the basic body 14 is between 1 ml and 750 ml, preferably between 10 ml and 250 ml. The cosmetic product 12 takes up a volume of advantageously between 50% and 95% of the internal volume 16, within the basic body 14.

As indicated above, a dispensing member 20 formed by a pump is advantageously fitted on the basic body 14, by snap-fastening or screwing. Sealing between the dispensing member 20 and the basic body 14 is ensured, even when the temperature and pressure are increased.

When the internal volume 16 is less than 10 ml, in particular less than 8 ml, the pump is advantageously replaced by a sealed cap which ensures sealing, even when the temperature and pressure are increased.

In this case, the bottle is advantageously composed of the following materials as a monolayer or as a multilayer: polyolefin, for example polypropylene or polyethylene, polyester, for example polyethylene terephthalate or polyethylene terephthalate ethylene, cycloolefin copolymers, polyamide, polycarbonate, polymethylpentene (TPX), polyether ether ketone (PEEK), polytetrafluoroethylene, glass.

The dispensing member 20 is based on the same materials or on polyoxymethylene (POM) or polybutylene terephthalate (PBT).

Advantageously, the dielectric constant is less than 4, in particular less than 2.6. The dielectric loss factor is less than $10^{-2}$.

In a further variant, the package 10 is a flexible package and the basic body 14 is formed for example from a bilayer material comprising an inner layer and an outer layer. The inner layer is made for example of polypropylene or polyethylene, the outer layer being made for example of polyethylene terephthalate.

In a further variant, the package 10 is a flexible package and the basic body 14 is formed from a monolayer material.

Figure 6:
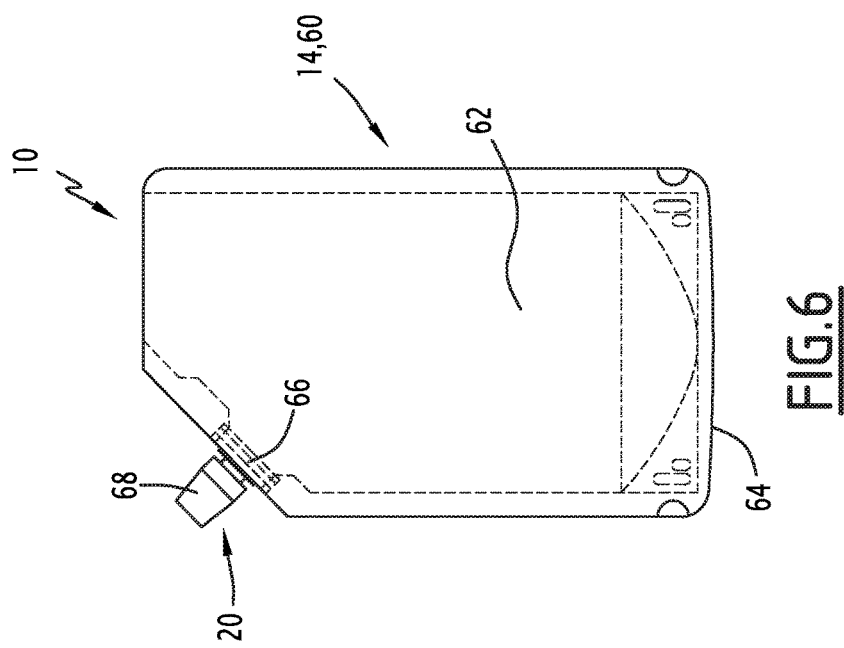
FIG. 6 illustrates yet another package according to the invention.

In the example shown in FIG. 6, the basic body 14 forms a flexible pouch 60 that is deformable to the touch, having two opposing faces 62 that delimit the internal volume 16.

Each face 62 is formed by a monolayer or preferably multilayer film. The layers of the multilayer film are joined together for example by extrusion and/or by lamination.

The structure of the multilayer film comprises at least two layers. At least one external layer allows printing and provides resistance to perforation. At least one internal layer is compatible with the packaged cosmetic product, is weldable, is resistant to the temperatures necessary for decontamination and is able to deform.

Advantageously, the materials that can be used are polyesters, polyamides and polyolefins.

Appropriate polyesters are formed by polyalkylene terephthalates having alkyl groups or radicals comprising 2 to 10 carbon atoms and polyalkylene terephthalates having alkyl groups or radicals containing 2 to 10 carbon atoms which are interrupted by 1 or 2 —O—. Further preferred polyesters are polyalkylene terephthalates having 5 alkyl groups or radicals containing 2 to 4 carbon atoms and preference is very particularly given to polyethylene terephthalates. These polyethylene terephthalates also include A-PET, PETP and the PETG mentioned or G-PET.

Examples of polyolefin materials are polyethylenes (PE), for example high density polyethylene (HDPE, density of greater than 0.944 g/cm3), medium density polyethylene (MDPE, density of 0.926 to 0.940 g/cm3), linear medium density polyethylene (LMDPE, density of 0.926 to 0.940 g/cm3), low density polyethylene (LDPE, density of 0.910 to 0.925 g/cm3) and linear low density polyethylene (LLDPE, density of 0.916 to 0.925 g/cm3), for example in the form of nonoriented sheets (PE sheet) or monoaxially or biaxially oriented sheets (oPE sheet), polypropylenes (PP), such as axially or biaxially oriented polypropylene (oPP sheet) or cast polypropylene (cPP sheet), amorphous or crystalline polypropylene or blends thereof or atactic or isotactic polypropylene or blends thereof, poly(1-butene), poly(3-methylbutene), poly(4 methylpentene) and copolymers thereof, then polyethylene with vinyl acetate, vinyl alcohol or acrylic acid, such as, for example, ionomer resins, such as copolymers of ethylene, of acrylic acid, of methacrylic acid, of acrylic esters, tetrafluoroethylene or polypropylene, in addition random copolymers, block copolymers or olefin polymer/elastomer blends. The polyolefin materials can also comprise cycloolefins as monomer of a homopolymer or of copolymers.

Preference is given to high density polyethylenes and to polypropylenes, and also to ionomers, for example known under the trade name Surlyn. Examples of polyamides (PA) for the plastics sheets are composed, for example, of polyamide 6, ε-caprolactam homopolymer (polycaprolactam); polyamide 11; polyamide 12, ω-lauryllactam homopolymer (polylauryllactam); polyamide 6,6, homopolycondensate of hexamethylenediamine and of adipic acid (poly(hexamethylene adipamide)); polyamide 6,10, homopolycondensate of hexamethylenediamine and of sebacic acid (poly(hexamethylene sebacamide)); polyamide 6,12, homopolycondensate of hexamethylenediamine and of dodecanedioic acid (poly (hexamethylene dodecanamide)) or polyamide 6-3-T, homopolycondensate of trimethylhexamethylenediamine and of terephthalic acid (poly(trimethylhexamethylene terephthalamide)), and blends thereof. The polyamide sheets are drawn monoaxially or biaxially (oPA).

The thicknesses of the layers can vary from 7 μm to 300 μm.

Treatments are possible: oxide deposition (SiOx, AlOx, etc.), microperforation, organic (epoxy, paraxylene, etc.) coating and orientation of the films.

Advantageously, the pouch 60 is provided with a bellows 64 in its bottom part and with a dispensing member 20 in its top part. In this example, the dispensing member 20 comprises a neck 66 that is more rigid than the pouch 60 and a removable cap 68 closing off the neck 66. A degassing system is advantageously provided in the dispensing member 20.

The pouch 60 does not contain any metallic elements.

The format of the pouch 60 is advantageously determined according to its volume and the surface area of its faces.

In the example shown in FIG. 6, the dimensions of the pouch 60 are defined for example by the following formula:

Surface area (cm2)=396.18×volume (cm3)−1702.4.

Thus, the volume of the pouch varies between 120 ml and 2 l for a surface area that varies between 310 $cm^2$ and 1500 $cm^2$. In a variant, the volume is between 1 ml and 750 ml, in particular between 10 ml and 250 ml.

The volume for filling with cosmetic product 12 is between 50% and 95% of the internal volume 16.

The dielectric constant of the materials forming the pouch 60 is preferably less than 2. The dielectric loss factor is preferably less than $10^{-2}$.

In a further variant, the package 10 is able to allow a single dose of cosmetic product 12 to be dispensed to at least one user.

It will thus be appreciated that the package 10 has improved resistance to temperatures, microwaves and internal pressures generated by the heating of the cosmetic product 12.

Figure 2:
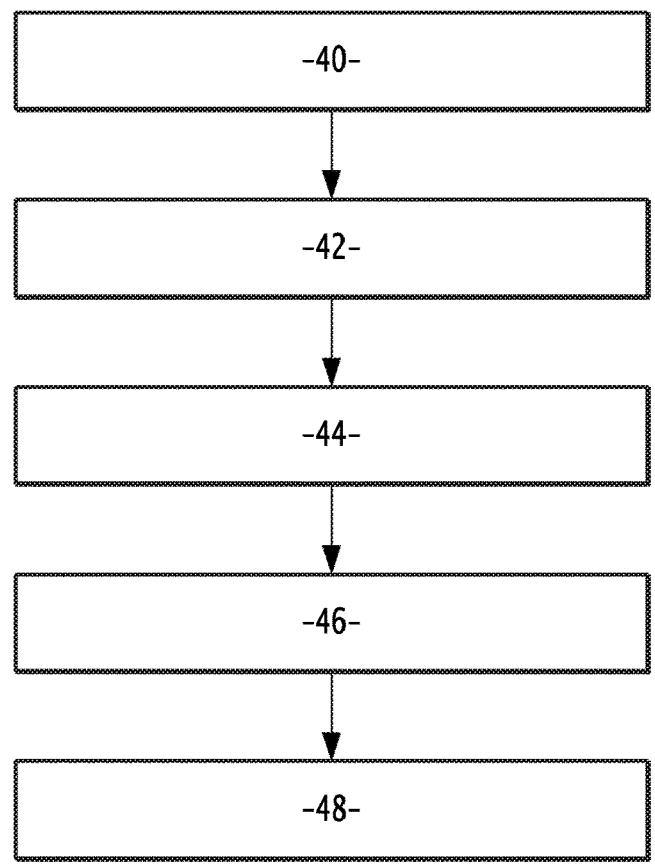
FIG. 2 is a flowchart showing the pasteurizing or sterilizing and packaging process according to the invention.

The process for decontaminating, in particular pasteurizing or sterilizing, and for packaging the cosmetic product 12 contained in the package 10 will now be described with reference to FIG. 2.

During an initial step 40, a cosmetic product 12 initially contained in a reservoir is introduced into the package 10, for example via the neck 18.

For example, the cosmetic product 12 is introduced into the package 10 by an assembly for introducing cosmetic product, not shown in the figures. The package 10 is then closed.

In the exemplary embodiment in FIG. 1, the sealed pump 26 is mounted on the neck 18, thereby closing the basic body 14 containing the cosmetic product 12. The pump 26 closes off in a sealed manner the cosmetic product 12 contained in the internal volume 16.

During a following step 42, the package 10 containing the cosmetic product 12 is placed in a microwave cavity, known per se. The microwave cavity has for example a thermal output power of between 100 W and 6000 W, preferably between 500 W and 6000 W, in particular between 1000 W and 2000 W.

The necessary power depends on the dielectric permittivity of the product and the package to be treated.

The microwave cavity is able to be controlled by a control assembly suitable for controlling the microwave cavity in order to effect a rise in temperature of the cosmetic product 12 contained in the package 10 by microwave heating to a decontamination temperature that corresponds to a pasteurization or sterilization temperature, and then to keep the cosmetic product 12 contained in the package 10 at the decontamination temperature for a decontamination time, able to bring about for example pasteurization or sterilization.

The microwave cavity is also able to emit electromagnetic waves at a frequency of between 800 MHz and 3000 MHz, for example between 2300 MHz and 2600 MHz, in particular 2450 MHz or 915 MHz.

During a following step 44, the package 10 containing the cosmetic product 12 is heated by the microwave cavity. The temperature of the cosmetic product 12 thus increases gradually by microwave heating until it reaches a predetermined decontamination, in particular pasteurization or sterilization, temperature. The sterilization temperature corresponds to a temperature at which, for a sufficient application time at this temperature, all of the microbial germs present within the cosmetic product 12 are eliminated in line with the sterilization thresholds defined above.

The pasteurization temperature corresponds to the temperature at which, for a sufficient application time at this temperature, the number of microbial germs present within the cosmetic product 12 decreases substantially in line with the pasteurization thresholds defined above.

The decontamination temperature is greater than or equal to 85° C., preferably between 85° C. and 150° C. In this exemplary embodiment, the microwave cavity emits a thermal power substantially equal to 500 W, corresponding to electromagnetic waves having a frequency substantially equal to 2450 MHz and the decontamination temperature is for example fixed at 85° C.

When the temperature of the cosmetic product 12 reaches the decontamination temperature, a fluid is set into circulation inside the microwave cavity during a subsequent step 46 so as to keep the temperature of the cosmetic product 12 constant.

The fluid is for example set into circulation in a thermally insulated pipe located within the microwave cavity or following the latter and is kept at the decontamination temperature by fluid heating means located within the cavity.

In an advantageous embodiment of the invention, the fluid is air. Thus, during step 46, the temperature of the cosmetic product 12 is kept at the decontamination temperature for a predetermined decontamination time, in particular for a pasteurization or sterilization time.

The sterilization time corresponds to a time for which, at the sterilization temperature, all of the microbial germs present within the cosmetic product 12 are eliminated in line with the sterilization thresholds defined above.

The pasteurization time corresponds to the time for which, at the pasteurization temperature, the number of microbial germs present within the cosmetic product 12 decreases substantially in line with the pasteurization thresholds defined above.

The decontamination time is greater than or equal to 2 minutes. In this exemplary embodiment, the pasteurization time is fixed at 2 minutes.

Advantageously, no electromagnetic radiation is emitted during this period.

In one variant, during step 46, the microwave cavity continues to emit electromagnetic radiation that is able to heat the cosmetic product 12, at the same time as the setting of the fluid into circulation inside the microwave cavity.

The joint activity of the electromagnetic radiation of the cavity and the conduction of heat by the fluid thus makes it possible to keep the temperature of the cosmetic product 12 at the decontamination temperature.

During this step 46, the microwave cavity emits for example a thermal power of between 1 W and 6000 W, in particular between 1000 W and 2000 W at the microwave frequencies defined above.

Figure 3:
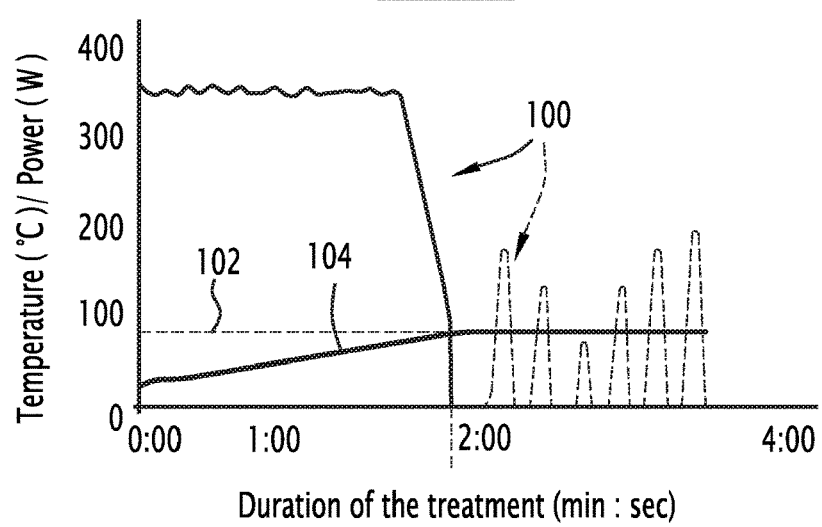
FIG. 3 illustrates the power output, the setpoint temperature and the temperature reached during the process in FIG. 2.

This radiation is emitted for example by discrete pulses. In FIG. 3, the curve 100 shows by way of a dotted line the power output, the curve 102 shows the setpoint temperature and the curve 104 shows the temperature measured inside the package 10.

At the end of the decontamination time, the cosmetic product 12 contained in the package 10 is cooled by forced cooling during a final step 48.

More specifically, the package 10 is introduced into a continuous cooling cell located at the outlet of the microwave cavity. In a variant, the process does not include a step 48 of forced cooling, the cosmetic product 12 then being cooled by contact of the package 10 with the ambient air when it leaves the microwave cavity.

The process according to the invention for decontaminating cosmetic products in their package and for packaging makes it possible to thermally treat the cosmetic product 12 without causing deterioration of the composition of this cosmetic product 12 or of the package 10. The decontamination is carried out directly on the packaged product 12 in a closed package, therefore not requiring any separate treatment of the package 10 or for packaging under a controlled atmosphere, apart from a possible check of the atmospheric humidity in the case of emulsions.

Moreover, the process according to the invention for decontaminating cosmetic products and for packaging can be implemented continuously in the flow of a line for packaging cosmetic products. This makes it possible to easily industrialize the process for sterilizing and packaging.

Finally, the process according to the invention for decontamination and for packaging makes it possible to obtain a decontaminated, in particular pasteurized or sterilized, cosmetic product the composition of which has a "microbiologically clean" state, such a state being able to be maintained at ambient temperature up to a predetermined date corresponding to the expiration date of the product.

It will thus be appreciated that the process according to the invention for decontaminating cosmetic products and for packaging makes it possible to obtain effective decontamination, while minimizing interaction with consumers' bodies and being easily industrializable.

Figure 5:
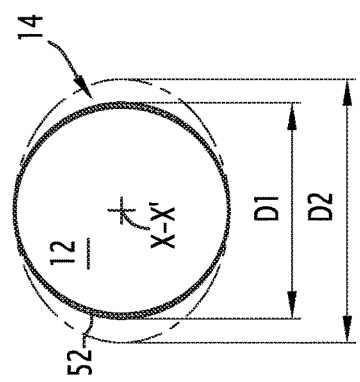
FIG. 5 illustrates a cross section through the package from FIG. 4.

Although the description of the process has been given with reference to a cosmetic product 12 contained in the package 10 illustrated in FIG. 1, or in other packages described in FIGS. 4 and 5, a person skilled in the art will of course understand that the process according to the invention for decontaminating cosmetic products and for packaging can be applied in the same way to any cosmetic product 12 contained in a package, regardless of the characteristics of this package.

Moreover, although the description of the cosmetic product 12 has been given with reference to a cleansing product for the skin, a person skilled in the art will understand that the invention can be applied in the same way to any cosmetic product liable to be contaminated by microbial development.

The package 10 containing the cosmetic product according to the invention resists an increase in pressure of at least 0.245 bar within the internal volume 16 together with a rise in the temperature of the product to above 85° C., in particular between 85° C. and 150° C., during a resistance time longer than two minutes.

The term the "package resists" means that the deformation of the package 10 is elastic and not plastic at the temperature reached.

Advantageously the package 10 is made by extrusion blow moulding to limit the thickness of the base 22.

Alternatively, the package 10 is made by injection blow moulding. This process supplies a package with an harder base 22.

The dielectric factor loss and dielectric constant for different material usable for the basic body 14 or the pouch 60 are listed in the following chart.

|  | Dielectric constant | Dielectric factor loss |
| --- | --- | --- |
| Polyethylene HD | 2.3 to 2.35 | 0.0003 |
| Polypropylene | 2.1 to 2.7 | 0.0005 to 0.0007 |
| Polyamide 6-6 | 3.6 to 4 | 0.014 |
| PET | 3.1 | 0.056 |
| Polycarbonate | 2.97 | 0.0001 to 0.0005 |
| Cyclo-olephine copolymer | 2.35 | 0.00007 to 0.0026 |
| Polymethylpentene (TPX) | 2.12 | 0.0002 |
| Polyether ether ketone (PEEK) | 3.2 | 0.003 |
| Poly tetrafluoroethylene | 2.1 | 0.0005 |
| PP-PET-PP Complex | 2.1 to 3.1 | 0.056 |
| PE-PET-PE Complex | 2.3 to 3.1 | 0.056 |
| Glass | 4 to 6 | 0.02 to 0.04 |

The invention claimed is:

1. A package containing a cosmetic product, the package comprising a basic body, a neck and a closure member or product dispensing member mounted on the neck, so as to form an internal volume containing the cosmetic product, wherein the package resists an increase in pressure of at least 0.245 bar within the internal volume together with a rise in the temperature of the product to above 85° C., the package undergoing no plastic deformation as a result of said increase in pressure together with said rise in the temperature,
the package comprising a shoulder joining the basic body to the neck, the basic body, the shoulder and the neck being formed integrally, the thickness of the shoulder being greater than the thickness of the central region of the basic body.

2. The package according to claim 1 wherein the basic body has a dielectric constant less than 4.

3. The package according to claim 2 wherein the basic body has a dielectric constant between 2.0 and 2.6.

4. The package according to claim 1, wherein the basic body has a dielectric loss factor less than $10^{-2}$.

5. The package according to claim 4, wherein the basic body has a dielectric loss factor between $10^{-4}$ and $10^{-3}$.

6. The package according to claim 1, wherein the cosmetic product contains no preserving agents.

7. The package according to claim 1, wherein the basic body exhibits symmetry of revolution about a central axis X-X'.

8. The package according to claim 7, wherein the basic body has a cylindrical, concave, convex, annular or spherical shape.

9. The package according to claim 1, wherein the basic body has an oval cross section the maximum diameter (D2) of which is less than or equal to 1.15 times the minimum diameter (D1).

10. The package according to claim 1, wherein the basic body is provided with a substantially concave or substantially convex base.

11. The package according to claim 10, wherein the thickness of the base is greater than 0.5 mm.

12. The package according to claim 11, wherein the thickness of the base is greater than 0.8 mm.

13. The package according to claim 10, wherein the base-is convex as seen from the inside of the basic body, the maximum depth (P1) of the base, measured from the supporting surface of the basic body towards the inside along the axis X-X', being greater than or equal to 0.02 times the minimum diameter (D1) of the cross section of the basic body.

14. The package according to claim 10, wherein the thickness of the lateral region, located next to the base, of the basic body is greater than the thickness of the central region of the basic body.

15. The package according to claim 14, wherein the thickness of the lateral region, located next to the base, of the basic body is greater than 1.2 times the thickness of the central region of the basic body.

16. The package according to claim 10, wherein the thickness of the base is greater than the thickness of the central region of the basic body.

17. The package according to claim 1, wherein the shoulder has a substantially rounded or frustoconical shape.

18. The package according to claim 1, wherein the basic body is composed of one or more materials chosen from polyolefins, polyesters, cycloolefin copolymers, polyamides, polycarbonates, polymethylpentene (TPX), polyether ether ketone (PEEK), polytetrafluoroethylene, or glass.

19. The package according to claim 1, wherein the basic body is formed from a material comprising a number of layers, the thickness of each layer being between 7 μm and 300 μm.

20. The package according to claim 1 wherein said rise in the temperature of the product is between 85° C. and 150° C.

21. The package according to claim 1, wherein the maximum thickness of the shoulder is greater than or equal to 1.2 times the maximum thickness in the central region of the basic body, when a snap-fastened pump is mounted on the neck.

22. A process for decontaminating cosmetic products comprising the following steps of:
providing a package containing a cosmetic product, the package being according to claim 1,
placing the containing the cosmetic product in a microwave cavity,
raising the temperature of the cosmetic product contained in the package to a decontamination temperature by microwave heating, and keeping the cosmetic product contained in the package at the decontamination temperature for a decontamination time suitable for reducing the number of bacteria present in the cosmetic product to below a decontamination threshold, the package undergoing no plastic deformation as a result of said increase in pressure together with said rise in the temperature, the package comprising a shoulder joining the basic body to the neck, the basic body, the shoulder and the neck being formed integrally, the thickness of the shoulder being greater than the thickness of the central region of the basic body.

23. The process according to claim 22, wherein, during the step of keeping the cosmetic product contained in the package at the decontamination temperature, a fluid is set into circulation inside the microwave cavity, the fluid being kept at the decontamination temperature by fluid heating means located within the microwave cavity.

24. The process according to claim 22 wherein the step-of keeping the cosmetic product contained in the package at the decontamination temperature includes the application of a microwave heating.

25. The process according to claim 22, wherein the package is sealed prior to the step of placing in the microwave cavity.

* * * * *